(12) United States Patent
Zhang et al.

(10) Patent No.: US 8,362,284 B2
(45) Date of Patent: Jan. 29, 2013

(54) METHOD OF ACHIEVING AND MAINTAINING A SPECIFIED ALKYLENE OXIDE PRODUCTION PARAMETER WITH A HIGH EFFICIENCY CATALYST

(75) Inventors: Liping Zhang, Lake Jackson, TX (US); Albert C. Liu, Charleston, WV (US); Michael Habenschuss, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 378 days.

(21) Appl. No.: 12/763,285

(22) Filed: Apr. 20, 2010

(65) Prior Publication Data

US 2010/0267972 A1    Oct. 21, 2010

Related U.S. Application Data

(60) Provisional application No. 61/171,284, filed on Apr. 21, 2009.

(51) Int. Cl.
*C07D 301/10* (2006.01)

(52) U.S. Cl. ...................................... 549/534

(58) Field of Classification Search ................... 549/534
See application file for complete search history.

(56) References Cited

U.S. PATENT DOCUMENTS

| | | |
|---|---|---|
| 4,759,313 A | 7/1988 | Dye |
| 4,761,394 A | 8/1988 | Lauritzen |
| 4,766,105 A | 8/1988 | Lauritzen |
| 4,769,047 A | 9/1988 | Dye |
| 4,808,738 A | 2/1989 | Lauritzen |
| 4,820,675 A | 4/1989 | Lauritzen |
| 4,831,162 A | 5/1989 | Nakajima |
| 4,874,739 A | 10/1989 | Boxhoorn |
| 4,874,879 A | 10/1989 | Lauritzen |
| 4,908,343 A | 3/1990 | Bhasin |
| 5,102,848 A | 4/1992 | Soo et al. |
| 5,143,877 A | 9/1992 | Geus |
| 5,145,824 A | 9/1992 | Buffum |
| 5,155,242 A | 10/1992 | Shankar |
| 5,228,484 A | 7/1993 | Johnson |
| 5,262,551 A | 11/1993 | Horrell et al. |
| 5,364,826 A | 11/1994 | Kemp |
| 5,380,697 A | 1/1995 | Matusz |
| 5,380,885 A | 1/1995 | Kemp |
| 5,387,751 A | 2/1995 | Hayden et al. |
| 5,418,202 A | 5/1995 | Evans |
| 5,447,897 A | 9/1995 | Kemp |
| 5,486,628 A | 1/1996 | Kemp |

(Continued)

FOREIGN PATENT DOCUMENTS

| | | |
|---|---|---|
| CA | 1286687 | 7/1991 |
| EP | 0357292 A1 | 3/1990 |

(Continued)

OTHER PUBLICATIONS

International Search Report and Written Opinion PCT/US2010/031673.

(Continued)

*Primary Examiner* — Taylor Victor Oh
(74) *Attorney, Agent, or Firm* — Hansen IP Law PLLC

(57) ABSTRACT

An improved method of operating an alkylene oxide production process to achieve and maintain a desired alkylene oxide production parameter is shown and described. The method comprises adjusting one of an overall catalyst chloriding effectiveness parameter or reaction temperature to obtain the desired alkylene oxide production parameter.

17 Claims, 9 Drawing Sheets

U.S. PATENT DOCUMENTS

| | | | |
|---|---|---|---|
| 5,504,053 A | 4/1996 | Chou et al. | |
| 5,519,152 A | 5/1996 | Gorcester | |
| 5,545,603 A | 8/1996 | Kemp | |
| 5,663,385 A | 9/1997 | Kemp | |
| 5,703,253 A | 12/1997 | Evans | |
| 5,719,299 A | 2/1998 | Raa | |
| 5,739,075 A | 4/1998 | Matusz | |
| 5,770,746 A * | 6/1998 | Cooker et al. | 549/534 |
| 5,801,259 A | 9/1998 | Kowaleski | |
| 5,840,932 A | 11/1998 | Evans | |
| 5,874,653 A | 2/1999 | Van Kruchten | |
| 5,929,259 A | 7/1999 | Lockemeyer | |
| 6,511,938 B1 | 1/2003 | Liu | |
| 7,615,655 B2 * | 11/2009 | Zhang et al. | 549/534 |
| 2004/0014999 A1 | 1/2004 | Chipman et al. | |
| 2006/0009647 A1 | 1/2006 | Yeates et al. | |
| 2009/0069583 A1 | 3/2009 | Rizkalla et al. | |
| 2010/0267974 A1 * | 10/2010 | Zhang et al. | 549/534 |

FOREIGN PATENT DOCUMENTS

| | | |
|---|---|---|
| EP | 266015 B1 | 12/1991 |
| EP | 0480537 A1 | 4/1992 |
| EP | 352850 | 1/1994 |
| EP | 480538 B1 | 9/1998 |
| EP | 1458698 B1 | 4/2005 |
| EP | 1458699 | 11/2005 |
| EP | 1458699 B1 | 11/2005 |
| GB | 1314613 | 4/1973 |
| WO | 9713579 | 4/1997 |
| WO | WO 03044002 | 5/2003 |

OTHER PUBLICATIONS

Notice of Opposition to European Patent No. 1,458,699 B1, filed with the European Patent Office (EPO) by The Dow Chemical Company, P.O. Box 1967, Midland, MI 4841-1967 (Aug. 3, 2006).

Notice of Opposition to European Patent No. 1,458,698 B1, filed with the European Patent Office (EPO) by The Dow Chemical Company, P.O. Box 1967, Midland, MI 4841-1967 (Jan. 18, 2006)

Reply in Opposition to European Patent No. 1,458,608 B1, filed with the European Patent Office (EPO) by The Dow Chemical Company, P.O. Box 1967, Midland, MI 4841-1967 (Aug. 22, 2008).

Berty, Chapter 8, Applied Industrial Catalysts, vol. 1 pp. 207-239 (1983).

* cited by examiner

US 8,362,284 B2

METHOD OF ACHIEVING AND MAINTAINING A SPECIFIED ALKYLENE OXIDE PRODUCTION PARAMETER WITH A HIGH EFFICIENCY CATALYST

CROSS-REFERENCE TO RELATED APPLICATIONS

This application claims the benefit of U.S. Provisional Application No. 61/171,284, filed on Apr. 21, 2009, the entirety of which is hereby incorporated by reference.

TECHNICAL FIELD

This disclosure relates generally to processes for making alkylene oxides, and more specifically, to an improved method of operating alkylene oxide production processes using high efficiency catalysts to achieve a specified alkylene oxide production rate.

BACKGROUND

Alkylene oxides are known for a multiplicity of utilities. Ethylene oxide, for example, is used to produce ethylene glycol, which is used as an automotive coolant, as antifreeze, and in preparing polyester fibers and resins, nonionic surfactants, glycol ethers, ethanolamines, and polyethylene polyether polyols. Propylene oxide is used to produce propylene glycol and polypropylene polyether polyols, which are used in polyurethane polymer applications.

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

$$7C_2H_4 + 6O_2 \rightarrow 6C_2H_4O + 2CO_2 + 2H_2O$$

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency at any point during its life, for example, under any set of reaction conditions as described in the Examples hereinafter, or by extrapolating lower efficiencies observed at two different oxygen conversions obtained by varying gas hourly space velocity to the limiting case of zero oxygen conversion, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. "Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than about 0.1%/ppmv) over a wide range of promoter concentrations, and this invariance is substantially unaltered as reaction temperature is changed during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced. Therefore, when using a conventional catalyst, for optimum efficiency, the gas phase promoter concentration in the feed can be chosen at a level at which the maximum efficiency can be maintained at relatively lower operating temperatures. Typically, the gas phase promoter concentration can remain substantially the same during the entire lifetime of a conventional catalyst. On the other hand, the reaction temperature may be adjusted to obtain a desired production rate without any substantial impact on efficiency due to non-optimal gas phase promoter concentration.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least about 0.2%/ppmv when operating away from the efficiency maximizing concentration). Thus, small changes in the promoter concentration can result in significant efficiency changes, and the efficiency exhibits a pronounced maximum, i.e., an optimum, at certain concentrations (or feed rates) of the gas phase promoter for a given reaction temperature and catalyst age. Moreover, the efficiency curves and the optimum gas phase promoter concentration tend to be strong functions of reaction temperature and are thus significantly affected if reaction temperature is varied, for example, to compensate for decreases in catalyst activity, (i.e., the change in efficiency with respect to a change in reaction temperature can be at least about 0.1%/° C. when operating away from the efficiency maximizing promoter concentrations for the selected temperatures). In addition, rhenium-promoted high efficiency catalysts have exhibited significant activity increases with increases in the gas phase promoter concentration in the feed, i.e., with increasing gas phase promoter concentration in the feed, temperature has to be decreased or the production rate will increase.

To address the strong influence of reaction temperature and gas phase promoter concentration on the efficiency of high efficiency catalysts, it has been proposed to use the temperature differential to first calculate the new gas phase promoter concentration. The gas phase promoter concentration changes are made whenever the reaction temperature is changed (U.S. Pat. No. 7,193,094; European Patent No. 1,458,699). However, this technique increases the complexity of the process and the controls that are required for automated operation. It can also result in excessive or insufficient gas phase promoter consumption and increase the sensitivity of the process to disturbances in reaction temperature. It also requires knowledge of a mathematical relationship between temperature and efficiency, which may be difficult or costly to obtain. Finally, the method is intended to maximize efficiency regardless of the alkylene oxide production rate. In many cases, it is desirable to operate the process at a specified alkylene oxide production rate, for example, in order to minimize feed rate disturbances to downstream units (e.g., alkylene glycol production units). Thus, a need has arisen for a process that addresses the foregoing issues.

SUMMARY

A process for manufacturing an alkylene oxide by reacting a feed gas comprising alkylene, oxygen, and at least one organic chloride over a high efficiency silver catalyst is provided. The process is operated at an initial overall catalyst chloriding effectiveness value and an initial reaction temperature to yield an initial value of an alkylene oxide production parameter. A desired value of the alkylene oxide production parameter is selected, and one selected from the overall catalyst chloriding effectiveness value of the feed gas and the reaction temperature is adjusted while maintaining the other of the overall catalyst chloriding effectiveness value and the reaction temperature at a substantially constant value to yield the desired value of the alkylene oxide production parameter. The overall catalyst chloriding effectiveness value is preferably adjusted within a selected range, and the reaction temperature is preferably adjusted within a selected range.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION

Figure 1:
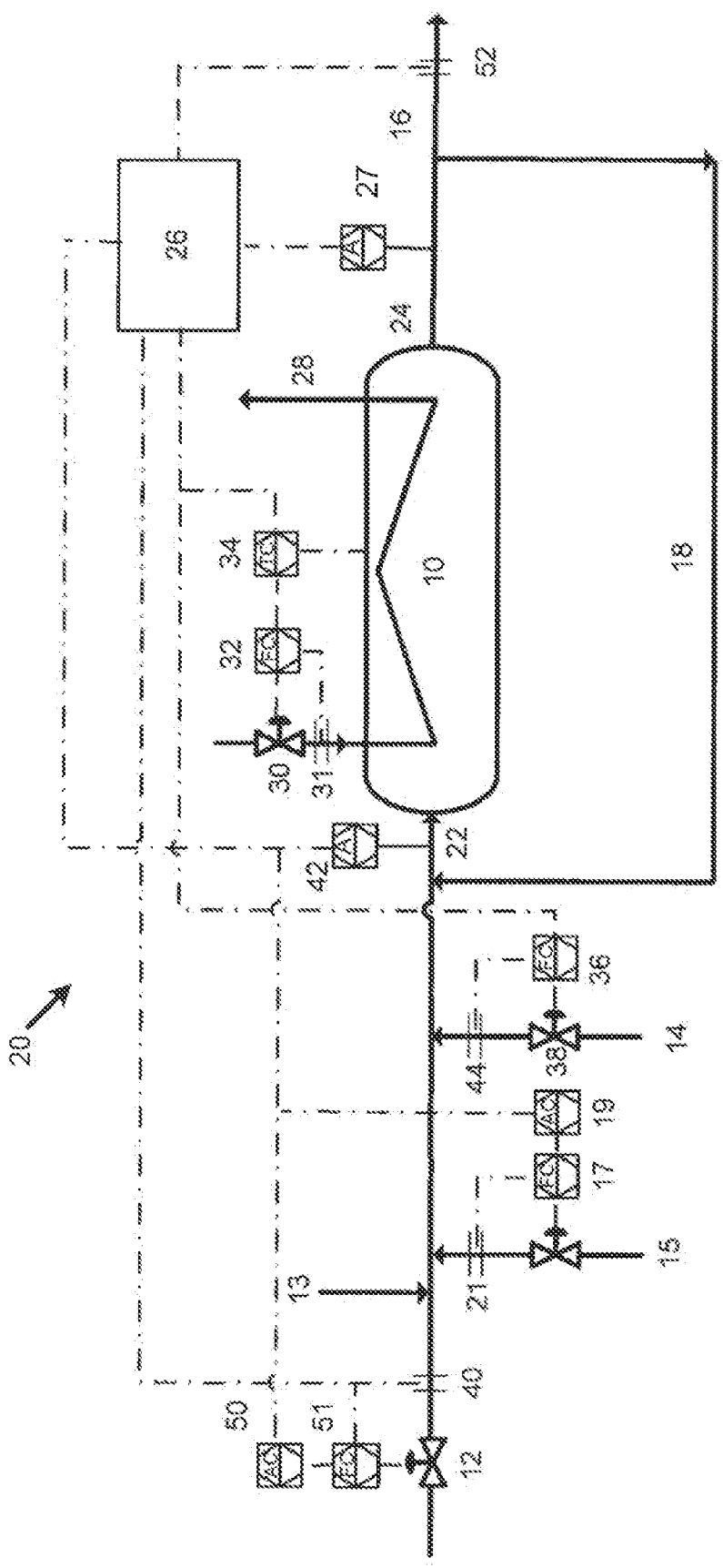
FIG. 1 is a process flow diagram depicting an embodiment of a process for making an alkylene oxide by epoxidizing an olefin over a high efficiency catalyst.

As discussed below, the present disclosure provides a method for achieving and maintaining a desired alkylene oxide production parameter, such as alkylene oxide yield, alkylene oxide reactor product concentration, alkylene conversion, oxygen conversion, or alkylene oxide production rate, by adjusting either an overall chloriding effectiveness parameter or reaction temperature. As will be explained, the use of the method allows the alkylene oxide production parameter to be easily adjusted without deviating significantly from a preferred initial operating condition, which includes, without limitation, an optimum operating condition.

In order to facilitate an understanding of the present disclosure, it is useful to define certain terms relating to catalyst and process performance. The activity of a catalyst in a fixed bed reactor is generally defined as the reaction rate towards the desired product per unit of catalyst volume in the reactor. The activity relates to both the total number of available active sites and the reaction rate of each site. The number of active sites can be reduced in several ways. For example, they can be reduced by coalescence of the silver particles, which reduces the surface area of the silver available for reaction. They can also be reduced by poisoning, for example by reaction with trace sulfur compounds in the reactor feed. The number of active sites can also be reduced by reaction with normal process constituents, such as by reaction with chloride compounds in the process stream to form silver chloride compounds, which are inactive towards the epoxidation reaction. The activity will also decline if the reaction rate goes down for at least some of the active sites (e.g., due to localized poisoning) independent of the total number of active sites. To compensate for the activity decline in order to maintain a given production rate, certain reaction conditions have to be changed to increase the overall production rate of the available active sites. For instance, reaction temperature is often raised to provide more energy to the active sites for this purpose. "Activity" can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reaction temperature is maintained substantially constant; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. One measure of the useful life of a catalyst is the length of time that reactants can be passed through the reaction system during which time acceptable productivity is obtained in light of all relevant factors. The "yield" of alkylene oxide refers to the net number of moles of alkylene oxide produced by the process divided by the net number of moles of olefin fed to the process for any given time period.

The term "alkylene oxide production parameter" is used herein to describe a variable that relates to the extent to which alkylene oxides are produced. Examples of alkylene oxide production parameters include, without limitation, alkylene oxide concentration, alkylene oxide yield, alkylene oxide production rate, alkylene oxide production rate/catalyst volume, alkylene conversion, and oxygen conversion. Thus, the alkylene oxide concentration relates to the alkylene oxide production rate because the production rate may be obtained by multiplying the alkylene oxide concentration and the net product flow rate. The alkylene oxide production rate/catalyst volume may be determined by dividing the production rate by the volume of the catalyst bed. The oxygen and alkylene conversions are related to the production of the alkylene oxide by the efficiency.

FIG. 1 illustrates a process 20 for making an alkylene oxide. Process 20 includes a reactor 10 comprising a tubular vessel with a catalyst bed disposed in it. Although depicted in a horizontal orientation in FIG. 1, commercial embodiments of reactor 10 are typically vertically oriented. Olefin (i.e., alkylene) feed stream 12 (which may also include saturated hydrocarbons, such as ethane, as an impurity) is combined with oxygen feed 15 and gas phase promoter feed 14 to define reactor feed stream 22 proximate the reactor inlet. Reactor outlet stream 24 includes the alkylene oxide ("AO") product, plus side products (e.g., $CO_2$, $H_2O$, and small amounts of saturated hydrocarbons), unreacted olefin, oxygen, and inerts. In commercial processes, the alkylene oxide product along with some water product is removed from the reactor outlet stream 24 in an alkylene oxide recovery unit (not shown). If desired, recycle stream 18 may also be provided to recycle unreacted olefins and oxygen, in which case net product stream 16 is also provided. However, if a recycle stream 18 is provided, a purge line is preferably provided to reduce the build up of impurities and/or side products such as argon and ethane. In addition, commercial processes also include a carbon dioxide removal step that is performed upstream of where recycle stream 18 combines with the fresh feed and enters the reactor 10.

The olefin comprising olefin feed stream 12 may be any olefin, including aromatic olefins and di-olefins, whether conjugated or not. However, preferred olefins are mono-olefins having the following formula:

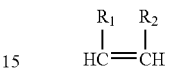

wherein, $R_1$ and $R_2$ are individually selected from the group consisting of hydrogen and alkyl radicals having from 1 to 6 carbon atoms. Propylene ($R_1$=$CH_3$, $R_2$=H) and ethylene ($R_1$=$R_2$=H) are more preferred, and ethylene is most preferred. Correspondingly, preferred alkylene oxides in reactor outlet stream 24 are of the formula:

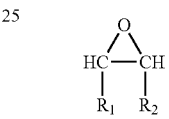

wherein, $R_1$ and $R_2$ are individually selected from the group consisting of hydrogen and alkyl radicals having from 1 to 6 carbon atoms. Propylene oxide ($R_1$=$CH_3$, $R_2$=H) and ethylene oxide ($R_1$=$R_2$=H) are more preferred, and ethylene oxide is most preferred.

Oxygen feed 15 may comprise substantially pure oxygen or air. If pure oxygen is used, ballast gases or diluents 13 such as nitrogen or methane may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, the oxygen concentration in reactor feed 22 will be at least about one (1) mole percent and preferably at least about two (2) mole percent. The oxygen concentration will generally be no more than about fifteen (15) mole percent and preferably no more than about twelve (12) mole percent. The ballast gas 13 (e.g., nitrogen or methane) is generally from about 50 mole percent to about 80 mole percent of the total composition of reactor feed stream 22. One reason that methane ballast gas is preferred over nitrogen is because, due to its higher heat capacity, methane facilitates the use of higher oxygen concentrations in the cycle, and therefore, improves both activity and efficiency.

The concentration of olefin in reactor feed stream 22 may vary over a wide range. However, it is preferably at least about eighteen (18) mole percent and more preferably at least about twenty (20) mole percent. The concentration of olefin in reactor feed stream 22 is preferably no greater than about 50 mole percent, and more preferably is no greater than about 40 mole percent.

When present, the carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in reactor feed 22 is generally no more than about 5 mole percent, preferably no more than about 3 mole percent, and even more preferably no more than about 2 mole percent of the total composition of reactor feed 22. Water may also be present in the feed gases, and may be present in concentrations that are preferably from 0 to no more than about two (2) mole percent.

The gas phase promoter is generally a compound that enhances the efficiency and/or activity of process 20 for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred as the gas phase promoter feed (stream 14). Using chlorohydrocarbon gas phase promoters as an example, it is believed that the ability of the promoter to enhance the performance (e.g., efficiency and/or activity) of process 20 for the desired alkylene oxide depends on the extent to which the gas phase promoter chlorinates the surface of the catalyst in reactor 10, for example, by depositing particular chlorine species such as atomic chlorine or chloride ions on the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins such as ethylene and propylene, are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22, when present, is from 0 to about 2 mole percent. Given the competing effects of the gas phase promoter and the chloride-removing hydrocarbons in reactor feed stream 22, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity $Z^*$ and represented by the following formula:

$$Z^* = \frac{\text{ethyl chloride equivalent } (ppmv)}{\text{ethane equivalent (mole percent)}} \quad (1)$$

wherein the ethyl chloride equivalent is the concentration in ppmv (which is equivalent to ppm mole) of ethyl chloride that provides substantially the same catalyst chloriding effectiveness of the organic chlorides present in reactor feed stream 22 at the concentrations of the organic chlorides in feed stream 22; and the ethane equivalent is the concentration of ethane in mole percent that provides substantially the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of $Z^*$ would then be 3 ppmv. As a further example, it has been found that for certain catalysts methyl chloride has about 10 times less the chloriding effectiveness of ethyl chloride. Therefore, for such catalysts the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppmv is 1.0×(vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of $Z^*$ would be 2*1+1+1*1=4 ppmv.

The ethane equivalent (i.e., the denominator in equation (1)) is the concentration of ethane in mole percent in reactor feed stream 22 plus the concentration of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppmv ethyl chloride equivalents is found to provide the same level of catalyst performance as 3.0 ppmv ethyl chloride equivalents with a similar feed composition but lacking ethane, then the ethane equivalent for 30.0 mole percent ethylene would be 0.30 mole percent. For an inlet reactor feed 22 having 30.0 mole percent ethylene and 0.3 mole percent ethane, the ethane equivalent will then be 0.6 mole percent. As another illustration, it has been found that for certain catalysts methane has about 500 times less the dechloriding effectiveness of ethane. Thus, for such catalysts the ethane equivalent for methane is 0.002×(methane concentration in mol %). For a hypothetical inlet reactor feed 22 having 30.0 mole percent ethylene and 0.1 mole percent ethane, the ethane equivalent then will be 0.4 mole percent. For an inlet reactor feed 22 having 30.0 mole percent ethylene, 50 mole percent methane, and 0.1 mole percent ethane, the ethane equivalent then will be 0.5 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the Z* calculation may be negligible.

Thus, given the foregoing relationships, in the case where reactor feed stream 22 includes ethylene, ethyl chloride, ethylene dichloride, vinyl chloride, and ethane, the overall catalyst chloriding effectiveness value of process 20 can be defined as follows:

$$Z^* = \frac{(ECL + 2^*EDC + VCL)}{(C_2H_6 + 0.01^*C_2H_4)} \quad (2)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C$=CH—Cl), respectively, in reactor feed stream 22. $C_2H_6$ and $C_2H_4$ are the concentrations in mole percent of ethane and ethylene, respectively, in reactor feed stream 22. It is important that the relative effectiveness of the gaseous chlorine-containing promoter and the hydrocarbon dechlorinating species also be measured under the reaction conditions which are being used in the process. Z* will preferably be maintained at a level that is no greater than about 20 and which is most preferably no greater than about 15. Z* is preferably at least about 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and methyl chloride, even though only ethyl chloride or ethylene dichloride is supplied to the system. The concentrations of ethyl chloride, vinyl chloride, and ethylene dichloride must be considered in calculating Z*.

The order in which the inlet gases (alkylene oxide and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in reactor feed stream 22 as it is introduced to the solid catalyst in reactor 10.

In the embodiment of FIG. 1, Reactor 10 is a fixed bed reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. The epoxidation reaction is generally exothermic. Thus, a coolant system 28 (e.g., a cooling jacket or a hydraulic circuit with a coolant fluid such as a heat transfer fluid or boiling water) is provided to regulate the temperature of reactor 10. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature.

It should be noted that the terms "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor coolant outlet temperature. In other embodiments, the reaction temperature may be the reactor coolant inlet temperature. The epoxidation reaction is carried out at a temperature that is preferably at least about 200° C., more preferably at least about 210° C., and most preferably at least about 220° C. Reaction temperatures of no more than 300° C. are preferred, and reaction temperatures of no more than about 290° C. are more preferred. Reaction temperatures of no more than about 280° C. are most preferred. The reactor pressure is selected based on the desired mass velocity and productivity and ranges generally from about 5 atm (506 kPa) to about 30 atm (3.0 MPa). The gas hourly space velocity (GHSV) is preferably greater than about 3000 $hr^{-1}$, more preferably greater than about 4,000 $hr^{-1}$, and most preferably greater than about 5,000 $hr^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379,134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, about 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least about 80 weight percent α-alumina and less than about 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof.

The alpha-alumina carrier prepared as described hereinabove preferably has a specific surface area of at least about 0.5 m$^2$/g, and more preferably, at least about 0.7 m$^2$/g. The surface area is typically less than about 10 m$^2$/g, and preferably, less than about 5 m$^2$/g. The alpha-alumina carrier preferably has a pore volume of at least about 0.3 cm$^3$/g, and more preferably, from about 0.4 cm$^3$/g to about 1.0 cm$^3$/g and a median pore diameter from about 1 to about 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than about 50 microns. In a preferred embodiment, the alpha-alumina carrier comprises zirconium silicate (zircon), present substantially as zirconium silicate in the finished carrier, more preferably, in an amount up to about 4 weight percent, calculated on the weight of the carrier.

Catalysts of this invention for the production of alkylene oxide, for example, ethylene oxide or propylene oxide may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140, incorporated herein by reference.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Typically, the amount of silver supported on the carrier is less than about 70 percent, and more preferably, less than about 50 percent by weight, based on the weight of the catalyst.

Although silver particle size in the finished catalyst is important, the preferred range is not narrow. A suitable silver particle size can be in the range of from about 10 to about 10,000 angstroms in diameter. A preferred silver particle size ranges from greater than about 100 to less than about 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst under reaction conditions.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst is not narrow and may vary over a wide range. The optimum alkali metal promoter concentration for a particular catalyst given the other carrier and catalyst properties will be dependent upon performance characteristics, such as catalyst efficiency, rate of catalyst aging and reaction temperature.

The concentration of alkali metal (based on the weight of cation, for example cesium) in the finished catalyst may vary from about 0.0005 to 1.0 wt. %, preferably from about 0.005 to 0.5 wt. %. The preferred amount of cation promoter deposited on or present on the surface of the carrier or catalyst generally lies between about 10 and about 4000, preferably about 15 and about 3000, and more preferably between about 20 and about 2500 ppm by weight of cation calculated on the total carrier material. Cation promoter amounts between about 50 and about 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from about 0.0001:1 to 10,000:1, preferably from about 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $SO_4^{-2}$, phosphates, for example, $PO_4^{-3}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

With certain highly efficient catalysts, the most preferred promoter comprises rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylene-diamine-tetraacetic acid (EDTA) or a suitable salt thereof.

The amount of anion promoters may vary widely, for example, from about 0.0005 to 2 wt. %, preferably from about 0.001 to 0.5 wt. % based on the total weight of the catalyst. When used, the rhenium component is often provided in an amount of at least about 1, say, at least about 5, for example, about 10 to 2000, often between 20 and 1000, ppmw calculated as the weight of rhenium based on the total weight of the catalyst.

Certain high-efficiency catalysts comprise at least one efficiency-enhancing salt of a member of a redox-half reaction pair which is employed in an epoxidation process in the presence of a gaseous nitrogen-containing component capable of forming a gaseous efficiency-enhancing member of a redox-half reaction pair under reaction conditions. This category of catalysts and epoxidation processes is not preferred for use with the methods and processes for manufacturing alkylene oxides that are disclosed and claimed herein. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). Such compounds, when associated with the catalyst as salts of members of a half reaction pair, are salts in which the anions are oxyanions, such as an oxyanion of a polyvalent atom; that is, the atom of the anion to which oxygen is bonded is capable of existing, when bonded to a dissimilar atom, in different valence states. As used herein, the term "salt" does not indicate that the anion and cation components of the salt be associated or bonded in the solid catalyst, but only that both components be present in some form in the catalyst under reaction conditions. Potassium is a typical cation, although sodium, rubidium and cesium may also be operable, and the typical anions are nitrate, nitrite and other anions capable of undergoing displacement or other chemical reaction and forming nitrate anions under epoxidation conditions. Typical salts include $KNO_3$ and $KNO_2$, with $KNO_3$ being most frequently used.

It is desirable that the silver and one or more solid promoters be relatively uniformly dispersed on the carrier. A preferred procedure for depositing silver catalytic material and one or more promoters comprises: (1) impregnating a carrier according to the present invention with a solution comprising a solvent or solubilizing agent, silver complex and one or more promoters, and (2) thereafter treating the impregnated carrier to convert the silver compound and effect deposition of silver and the promoter(s) onto the exterior and interior pore surfaces of the carrier. Silver and promoter depositions are generally accomplished by heating the solution containing carrier at elevated temperatures to evaporate the liquid within the carrier and effect deposition of the silver and promoters onto the interior and exterior carrier surfaces. The temperature of the heating step is high enough to reduce any silver compounds to metallic silver. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

Figure 2:
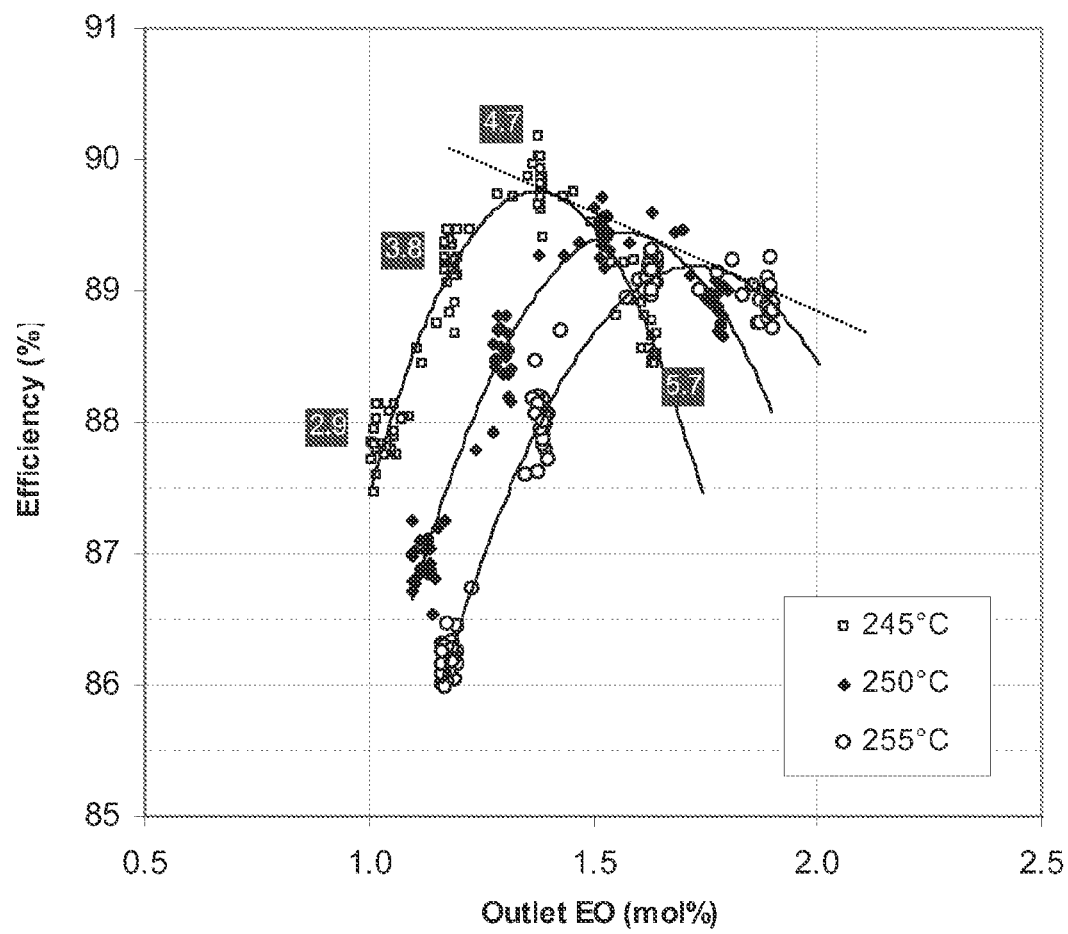
FIG. 2 is a series of curves depicting relationships between catalyst efficiency (selectivity) and reactor outlet ethylene oxide concentration at three different temperatures and four different overall catalyst chloriding effectiveness parameter values.

As is known in the art, the yield of alkylene oxide depends on the rate of olefin consumption, and the rates of competing side reactions. With conventional catalysts, a desired rate of alkylene oxide production can be achieved by varying reaction temperature without sacrificing efficiency substantially. However, in making such an adjustment with high efficiency catalysts, efficiency is typically dependent on both the overall catalyst chloriding effectiveness and the reaction temperature. Thus, a change that would increase the rate of olefin consumption may be accompanied by a corresponding decrease in efficiency. It is generally desirable to maximize efficiency to minimize the raw material consumption and the generation of unwanted byproducts (carbon dioxide and water). Because efficiency varies with both overall catalyst chloriding effectiveness and reaction temperature, both variables must typically be varied in order to obtain a desired alkylene oxide production parameter. FIG. 2 illustrates this phenomenon. The figure depicts reactor outlet ethylene oxide concentration and efficiency (selectivity) data for a high efficiency, rhenium-promoted silver catalyst operated at three different reaction temperatures (245° C., 250° C., and 255° C.) at four different values of the overall catalyst chloriding effectiveness parameter $Z^*$ (2.9, 3.8, 4.7, and 5.7, as shown in the squares in FIG. 2) which were obtained by varying the inlet concentration of ethyl chloride. The same values of $Z^*$ were used for all three temperatures, but for simplicity only the graph for 245° C. is labeled with the $Z^*$ values. The temperatures increase moving from the top left of the graph to the bottom right of the graph, and each curve is generally parabolic. Thus, at a $Z^*$ value of 4.7, an outlet ethylene oxide concentration of about 1.4 mole percent is achieved at an efficiency of 89.8% when the reaction temperature is 245° C. However, for the same reactor outlet ethylene oxide concentration, the efficiency drops off to about 89.0% when the temperature is increased to 250° C., and drops further to about 88.0% when the temperature is increased to 255° C. As the figure also illustrates, if after operating at an ethylene oxide reactor outlet concentration of 1.4 mole percent at 245° C., it is desired to increase the amount of ethylene oxide to about 1.7 mole percent, simply increasing $Z^*$ to 5.7 without increasing the reaction temperature will produce the desired yield. However, the efficiency will drop off to about 88.5%. As a result, certain known methods such as those described in U.S. Pat. No. 7,193,094 emphasize the need to simultaneously change the overall catalyst chloriding effectiveness whenever reaction temperature is changed.

It has been discovered that within certain ranges of overall catalyst chloriding effectiveness and reaction temperature, the relationship between efficiency and reaction temperature, as well as between efficiency and overall catalyst chloriding effectiveness, is relatively flat, whereas the reaction rate changes monotonically with changes in gas phase chloriding level. As a result, for a given catalyst activity and within a certain range of overall catalyst chloriding effectiveness values and reaction temperatures, alkylene oxide production parameters such as the concentration of alkylene oxide in the reactor outlet stream 24 can be adjusted and maintained without substantially sacrificing efficiency by adjusting one of the overall catalyst chloriding effectiveness or the reaction temperature while holding the other variable constant. The adjustments to reaction temperature or overall catalyst chloriding effectiveness are preferably made while holding the reactor inlet alkylene concentration at a substantially constant value and even more preferably while also operating the alkylene oxide production process at a substantially fixed process condition. The fixed process condition is one in which at least one variable selected from the group consisting of pressure, reactor inlet oxygen concentration, reactor inlet carbon dioxide concentration, and gas hourly space velocity is held at a substantially constant value. In one exemplary embodiment, each of these variables is held at a substantially constant value.

Figure 3:
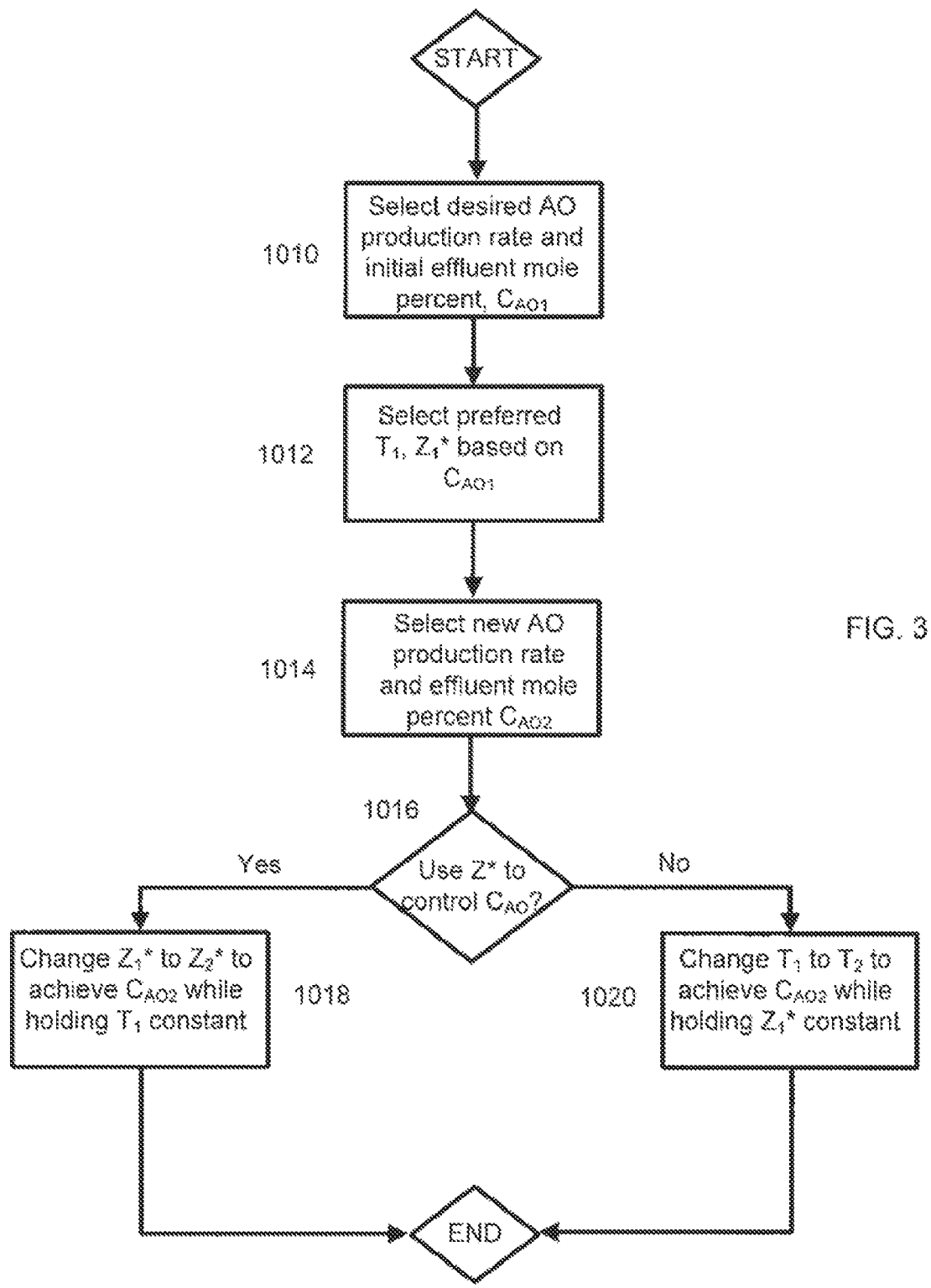
FIG. 3 is a flow chart depicting an embodiment of a method for operating the process of FIG. 1 to achieve and maintain a desired alkylene oxide production rate and reactor outlet alkylene oxide concentration.

An embodiment of an improved method for achieving and maintaining a desired alkylene oxide yield is illustrated in FIG. 3. In accordance with the method, a preferred initial operating condition, comprising an initial value of an alkylene oxide production parameter (which in FIG. 3 is reactor outlet alkylene oxide concentration ($C_{AO1}$)), initial reaction temperature ($T_1$) and initial overall chloriding effectiveness value ($Z_1^*$), is selected. According to the selected variables, a preferred initial efficiency ($E_1$) is obtained. In the embodiment illustrated in FIG. 3, an initial alkylene oxide production rate and a corresponding initial reactor outlet concentration ($C_{AO1}$) of alkylene oxide are first selected (step 1010). Alternatively, a desired alkylene oxide outlet concentration $C_{AO1}$ may be selected without selecting a target production rate. However, if a target production rate is selected, $C_{AO1}$ may be calculated from the selected alkylene oxide production mass flow rate, $F_{AO}$ and the total inlet volumetric flow rate (V) at standard temperature and pressure (T=273.15° K., P=1 atm). In accordance with one method, the change in alkylene oxide concentration as a mole percentage ($\Delta AO$ %) is first calculated as follows:

$$\Delta AO\% = (F_{AO}/MW_{AO})(RT/P)(100/V) \quad (3)$$

wherein $MW_{AO}$ is the molecular weight of the alkylene oxide (e.g., 44.05 g/gmol for ethylene oxide), and R is the ideal gas constant. Based on $\Delta AO$ % and the reactor inlet concentration of the alkylene oxide ($C_{AO\,Inlet}$), the following two equations are then simultaneously solved to obtain the outlet concentration of alkylene oxide in mole percent ($C_{AO1}$):

$$\text{Shrink Factor}(SF) = (200 + C_{AO\,Inlet})/(200 + C_{AO1}). \quad (4)$$

$$\Delta AO\% = SF^* C_{AO1} - C_{AO\,Inlet} \quad (5)$$

The "Shrink Factor" represents the net volumetric reduction occurring due to the production of the alkylene oxide. For example, in the case of ethylene oxide production, for every mole of ethylene oxide produced, there is a net reduction of 0.5 moles of total gas resulting in a corresponding reduction in the volumetric flow rate.

Based on the initial reactor outlet concentration of alkylene oxide ($C_{AO1}$), an initial reaction temperature ($T_1$) and overall catalyst chloriding effectiveness parameter value ($Z_1^*$) are selected in step 1012. Alternatively, in step 1010, one of $T_1$ and $Z_1^*$ can be selected, and $C_{AO1}$ and the other of $T_1$ and $Z_1^*$ can be selected in step 1012 based on the one of $T_1$ and $Z_1^*$ selected in step 1010. In either case, the combination of $C_{AO1}$, the initial reaction temperature $T_1$ and initial overall catalyst chloriding effectiveness parameter $Z_1^*$ are preferably selected based on a preferred initial operating condition. In one embodiment, the preferred initial operating condition is selected to maintain the first derivative of efficiency with respect to reactor outlet alkylene oxide concentration at constant temperature, reactor inlet alkylene concentration, and a fixed process condition ($\partial E/\partial C_{AO}$) within a specified range. The fixed process condition is one in which at least one variable selected from the group consisting of pressure, reactor inlet oxygen concentration, reactor inlet carbon dioxide concentration, and gas hourly space velocity is held at a constant value. In one preferred embodiment, the fixed process condition is a condition at which each of pressure, reactor inlet oxygen concentration, reactor inlet carbon dioxide concentration and gas hourly space velocity is held constant. In another embodiment, the preferred operating condition is selected to provide a reactor outlet alkylene oxide concentration ($C_{AO1}$) that is higher than the efficiency-maximizing alkylene oxide concentration at an epoxidation temperature. In still another embodiment, the preferred operating condition is selected to provide an overall chloriding effectiveness value that is higher than the efficiency-maximizing overall chloriding effectiveness value at the same reaction temperature. In yet another embodiment, the initial overall catalyst chloriding effectiveness value $Z_1^*$ and the initial reaction temperature $T_1$ are selected to maximize efficiency toward the alkylene oxide at the desired reactor outlet alkylene oxide concentration, $C_{AO1}$. Other optimization methods and other methods of selecting a preferred initial operating condition may also be used. For example, it may be desired to operate process 20 at the maximum catalyst efficiency for a given selected initial reaction temperature $T_1$ regardless of the alkylene oxide concentration in the reactor outlet 24. In addition, an efficiency maximizing scheme may be chosen by operating at the minimum obtainable reaction temperature (based on the capacity of coolant circuit 28) and by selecting the value of $Z_1^*$ that obtains the maximum efficiency. Alternatively, reactor outlet alkylene oxide concentration may be maximized regardless of the efficiency (as limited by the maximum temperature the reactor can withstand). Techniques such as the foregoing can be used to select $T_1$ and $Z_1^*$ and will be discussed further below.

After the preferred initial operating condition ($C_{AO1}$, $T_1$, $Z_1^*$, $E_1$) is selected in steps 1010 and 1012, if it is then desired to adjust the alkylene oxide production parameter (e.g., the alkylene oxide production rate and/or the concentration of alkylene oxide in the reactor outlet), a new value (concentration, $C_{AO2}$) is selected (step 1014). In order to achieve the desired value, either $Z^*$ or reaction temperature is selected as the variable that will be manipulated. If $Z^*$ is selected, in step 1018 $Z^*$ is changed from $Z_1^*$ to $Z_2^*$ (e.g., by increasing the flow of the organic chloride gas phase promoter in stream 14) while holding $T_1$ constant. If reaction temperature T is selected, in step 1020 the temperature is changed from $T_1$ to $T_2$ (e.g., by reducing the flow rate of coolant in cooling circuit 28 or by increasing the steam drum pressure in a boiling water cooled system) while holding $Z_1^*$ constant. If an increase in the production of alkylene oxide is desired, $Z^*$ will be increased in step 1018 or T will be increased in step 1020. Conversely, if a decrease in the production of alkylene oxide is desired, $Z^*$ will be decreased in step 1018 or T will be decreased in step 1020. In manipulating T or $Z^*$ it is preferred to operate the alkylene oxide production process at a substantially constant reactor inlet alkylene concentration, and it is further preferred to also operate the process at a substantially fixed process condition in which at least one variable selected from the group consisting of pressure, reactor inlet oxygen concentration, reactor inlet carbon dioxide concentration, and gas hourly space velocity is held at a substantially constant value. In one exemplary embodiment, each of these variables is held at a substantially constant value.

Thus, in contrast to methods such as those described in U.S. Pat. No. 7,193,094, the method of FIG. 3 avoids the complexity involved in simultaneously manipulating reaction temperature and gas-phase promoter concentration, which introduces complexity into the operation and control of the process and can cause or exacerbate the effect of process disturbances.

The changes in $Z^*$ and T described in FIG. 3 are generally of a magnitude that is sufficient to change the rate of reaction to the extent needed to obtain a desired yield (and/or reactor outlet concentration) of alkylene oxide. The changes in $Z^*$ (i.e., $\Delta Z^*$) made in step 1018 are preferably no greater than about 2, more preferably no greater than about 1.5, even more preferably no greater than about 1.3 and most preferably no greater than about 1.0. The changes in reaction temperature T (i.e., $\Delta T$) made in step 1020 are preferably no greater than about 10° C., more preferably no greater than about 7° C., even more preferably no greater than about 5° C., and most preferably no greater than about 2° C. In certain embodiments, the changes in $Z^*$ in step 1018 and T in step 1020 result in a change in efficiency ($\Delta E$) that is preferably no greater than about 1.0%, more preferably no greater than about 0.5% and most preferably no greater than about 0.3%.

As indicated previously, process 20 is preferably operated to ensure that the catalyst efficiency remains relatively flat with respect to overall catalyst chloriding effectiveness and reaction temperature. To ensure operation in this region, $Z^*$ and T are preferably maintained within respective selected ranges. Thus, $Z^*$ will preferably be maintained at a level that is no greater than about 20 and which is most preferably no greater than about 15. $Z^*$ is preferably at least about 1. In addition, the reaction temperature is preferably at least about 200° C., more preferably at least about 210° C., and most preferably at least about 220° C. Reaction temperatures of no more than 300° C. are preferred, and reaction temperatures of no more than about 290° C. are more preferred. Reaction temperatures of no more than about 280° C. are most preferred.

As is known in the art, the age of a catalyst can affect its activity due to a number of mechanisms. See Bartholomew, C. H., "Mechanisms of Catalyst Deactivation," *Applied Catalysis*, A: General (2001), 212(1-2), 17-60. As the activity changes, the relationship between efficiency, $Z^*$ and reaction temperature may also change. Thus, the method of FIG. 3 is preferably performed over a relatively narrow catalyst age range that provides a substantially constant catalyst activity. However, fresh, middle-of-life, and aged catalysts may be used. Catalyst age may be expressed in a number of ways such as days on stream or the ratio of cumulative product output (e.g., in metric kilotons, "kt") divided by packed reactor volume (e.g., in cubic meters). The methods described herein are carried out on a catalyst having an age that is preferably no greater than about 10 kt alkylene oxide/$m^3$ catalyst, more preferably no greater than about 8 kt alkylene oxide/$m^3$ catalyst, even more preferably, no greater than about 6 kt alkylene oxide/$m^3$ catalyst, and most preferably no greater than about 4 kt alkylene oxide/$m^3$ catalyst.

As mentioned previously, in step 1012 of the method of FIG. 3, the initial reaction temperature ($T_1$) and initial overall catalyst chloriding effectiveness value ($Z_1^*$) are preferably selected to obtain a preferred initial operating condition. Methods of selecting a preferred initial operating condition (e.g., $T_1$, $Z_1^*$, $C_{AO1}$, $E_1$) will now be described. By way of illustration, the alkylene oxide production parameter used to illustrate the method is alkylene oxide concentration, $C_{AO}$. However, other alkylene oxide production parameters may be used.

Figure 7A:
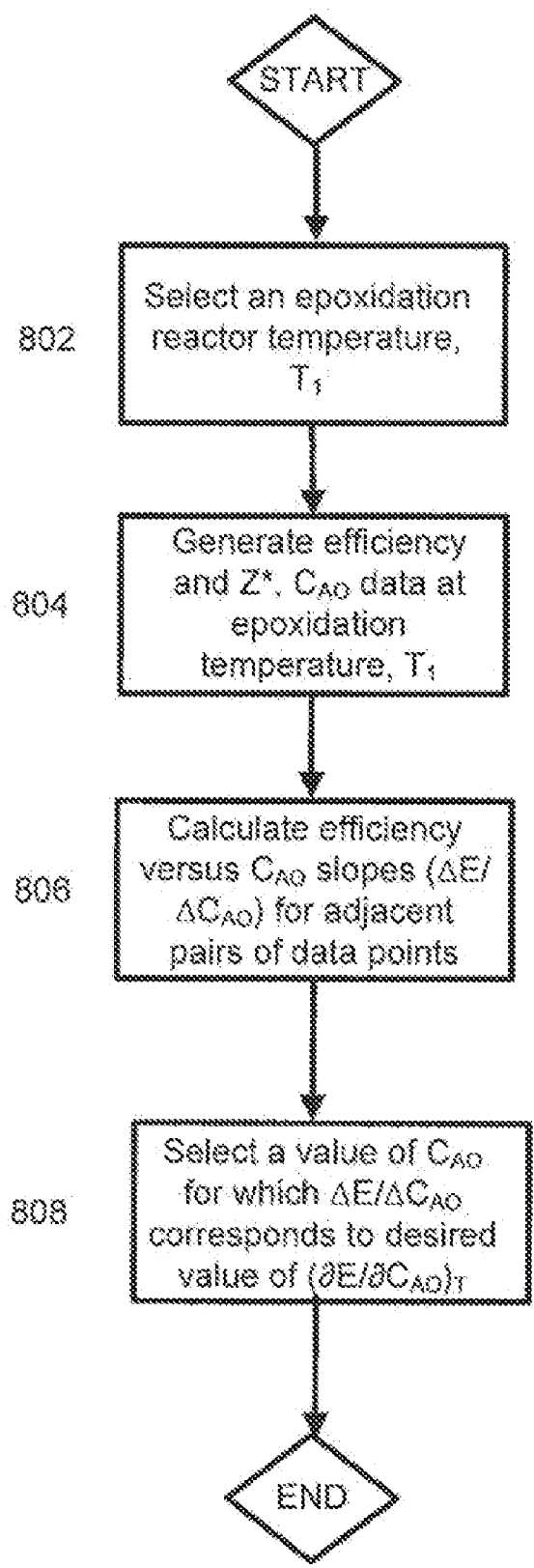
FIG. 7A is a flow chart depicting a first exemplary method of selecting a preferred initial operating condition of an alkylene oxide production process.

In accordance with a first exemplary embodiment, $T_1$ and $Z_1^*$ are selected to correspond to a slope of efficiency versus reactor outlet alkylene oxide concentration that is within a selected range of values. The slope is the slope of efficiency versus reactor outlet alkylene oxide concentration as $Z^*$ is varied at constant temperature while holding reactor inlet alkylene concentration constant and operating at a fixed process condition. The fixed process condition is a condition at which at least one variable selected from the group consisting of reactor inlet oxygen concentration, reactor inlet carbon dioxide concentration, reactor pressure, and gas hourly space velocity is held constant. In a preferred embodiment, the fixed process condition is one at which each of these variables is held constant. The slope is preferably no greater than about −1 percent efficiency/mole percent alkylene oxide, more preferably no greater than about −1.5 percent efficiency/mole percent alkylene oxide, and even more preferably no greater than about −2 percent efficiency/mole percent alkylene oxide. The slope is preferably at least about −5 percent efficiency/mole percent alkylene oxide, more preferably at least about −4.5 percent efficiency/mole percent alkylene oxide, and even more preferably at least about −4 percent efficiency/mole percent alkylene oxide. A slope of about −3 percent efficiency/mole percent alkylene oxide is especially preferred. Referring to FIG. 7A, a method of implementing the exemplary embodiment is depicted. In accordance with the method, in step 802, a first selected reaction temperature, $T_1$ is selected to be an epoxidation reaction temperature that is at least about 200° C., more preferably at least about 210° C., and most preferably at least about 220° C. $T_1$ is preferably no greater than about 300° C., more preferably no greater than about 290° C., and most preferably no greater than about 280° C. In step 804, a first set of efficiency and $C_{AO}$ data is generated by varying $Z^*$ and measuring $C_{AO}$ and determining the efficiency at the various $Z^*$ values while holding the reaction temperature at the first selected reaction temperature $T_1$ and while holding reactor inlet alkylene concentration constant at a fixed process condition, as described above.

In step 806, the linear slopes defined by adjacent pairs of efficiency values and $C_{AO}$ values (e.g., $\Delta E/\Delta C_{AO}$) are determined at $T_1$. In step 808, a value of $C_{AO1}$ is selected at which $\Delta E/\Delta C_{AO}$ corresponds to a slope $(\partial E/\partial C_{AO})_T$ as described above. $Z_1^*$ can then be determined from the collected data (e.g., by interpolation) based on the selected value of $\Delta E/\Delta C_{AO}$.

Figure 7B:
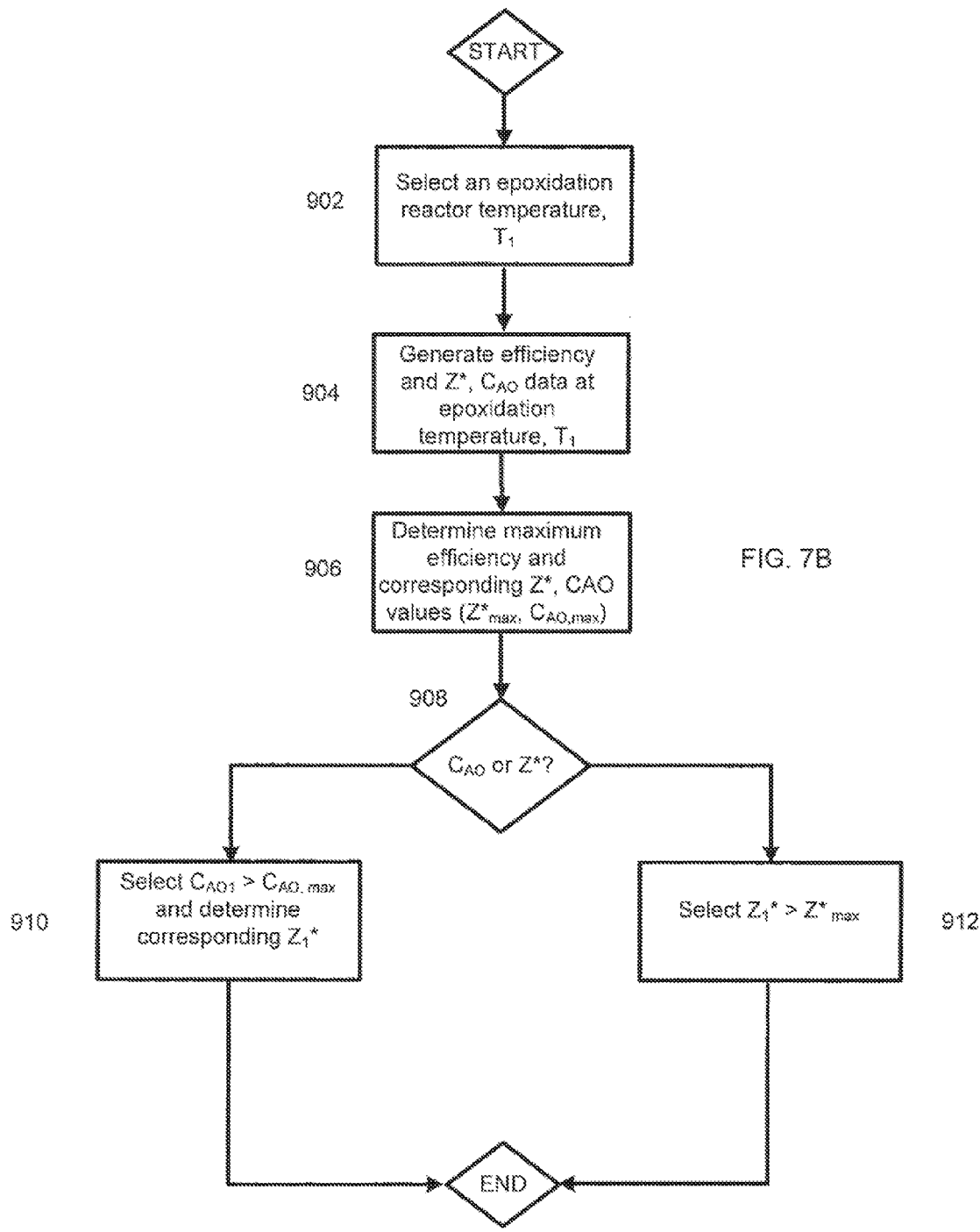
FIG. 7B is a flow chart depicting a second exemplary method of selecting a preferred initial operating condition of an alkylene oxide production process.

In accordance with another exemplary embodiment, the preferred initial operating condition is selected to provide an efficiency that is less than the maximum efficiency. In a preferred implementation, the initial reactor outlet alkylene oxide concentration ($C_{AO1}$) is selected to be greater than the efficiency-maximizing concentration. Referring to FIG. 7B, a method of implementing the exemplary embodiment is depicted. In accordance with the method, in step 902 $T_1$ is selected as described in the previous embodiment. In step 904, efficiency values are determined in the same manner as described above for step 804 in FIG. 7A. In step 906, a maximum efficiency value for $T_1$ is determined and the corresponding efficiency-maximizing $Z^*$ and $C_{AO}$ values ($Z^*_{max}$ and $C_{AO\ max}$) are determined In one illustrative example, the maximum efficiency value is determined by plotting the collected values of efficiency versus $Z^*$ and/or $C_{AO}$ and graphically and/or numerically determining (e.g., via curve-fitting, modeling, and/or interpolation) the maximum efficiency, $Z^*_{max}$ and/or $C_{AO,\ max}$. In step 908, it is determined whether to select $Z_1^*$ based on the efficiency maximizing value of $Z^*$ (i.e., $Z^*_{max}$) or to first select a reactor outlet alkylene oxide concentration $C_{AO1}$ based on the efficiency maximizing value of $C_{AO}$ (i.e., $C_{AO\ max}$). If the latter method is selected, $C_{AO1}$ is selected to be greater than $C_{AOmax}$ in step 910. $C_{AO1}$ is preferably at least about one percent greater than $C_{AOmax}$ (i.e., at least about 1.01 $C_{AOmax}$), more preferably at least about 5 percent greater than $C_{AOmax}$, and even more preferably at least about 10 percent greater than $C_{AO\ max}$. $C_{AO1}$ is preferably no more than about 25 percent greater than $C_{AO\ max}$ (i.e., no more than about 1.25 $C_{AOmax}$), more preferably no more than about 20 percent greater than $C_{AOmax}$, and even more preferably no more than about 15 percent greater than $C_{AO,\ max}$. Based on the selected value of $C_{AO1}$, the necessary value of $Z_1^*$ to achieve $C_{AO1}$ can then be determined from the collected data.

If $C_{AO}$ is not used to determine $Z_1^*$, then in step 912 $Z_1^*$ is selected to be greater than the efficiency-maximizing value of $Z^*$ (i.e., $Z^*_{max}$). $Z_1^*$ is preferably at least about one percent greater than $Z^*_{max}$, (i.e., at least about 1.01 $Z^*_{max}$) more preferably at least about 5 percent greater than $Z^*_{max}$, and more preferably at least about 10 percent greater than $Z^*_{max}$. $Z_1^*$ is preferably not more than about 25 percent greater than $Z^*_{max}$ (i.e., not more than 1.25 $Z^*_{max}$), more preferably not more than about 20 percent greater than $Z^*_{max}$, and even more preferably not more than about 15 percent greater than $Z^*_{max}$. The selection of $Z_1^*$, and $T_1$ will determine $C_{AO1}$.

Referring again to FIG. 3, in accordance with yet another exemplary embodiment, after selecting a desired initial alkylene oxide production rate or outlet concentration ($C_{AO1}$) in step 1010, the preferred initial values of T and $Z^*$ (i.e., $T_1$, $Z_1^*$) are selected to obtain the maximum (optimum) efficiency at the desired initial reactor outlet concentration of alkylene oxide, $C_{AO1}$. As shown in FIG. 2, it has been found that the relationship between efficiency and alkylene oxide concentration when varying $Z^*$ at a constant temperature (while also holding reactor inlet alkylene concentration constant and operating at a fixed process condition) defines a curve having the shape of a downward opening parabola, and that increasing the reaction temperature shifts the parabola downward and to the right. Increasing $Z^*$ at constant temperature (while also holding reactor inlet alkylene constant and operating at a fixed process condition) moves the process along the efficiency vs. ethylene oxide curve in the direction of increasing ethylene oxide concentration. As mentioned previously, the fixed process condition is one at which at least one of reactor inlet oxygen concentration, reactor inlet carbon dioxide concentration, reactor pressure, and gas hourly space velocity is held constant. More preferably, each of these variables is held constant. It has also been found that the optimum (efficiency-maximizing) combinations of reaction temperature and overall catalyst chloriding effectiveness values over a range of alkylene oxide production rates are defined by a line that is tangent to the series of parabolic-shaped curves described above which define the relationship between efficiency and alkylene oxide concentration at various temperatures. Thus, for a given reactor inlet alkylene concentration and fixed process condition (as defined above), a selected alkylene oxide concentration corresponds to an efficiency-maximizing combination of reaction temperature and overall chloriding effectiveness. In other words, the alkylene oxide concentration corresponds to a point on the tangent line and to a temperature that corresponds to the efficiency vs. alkylene oxide concentration parabola to which the line is tangent at the selected alkylene oxide concentration. The selected alkylene oxide concentration also corresponds to a specific efficiency-maximizing value of $Z^*$ at the specified concentration. Referring again to FIG. 2, the indicated tangent line intersects the 245° C. (upper left) parabola at about 1.4 mole percent ethylene oxide and about 89.8% efficiency. Thus, for a 1.4 mole percent ethylene oxide concentration, the optimum efficiency will be 89.8%, the optimum temperature will be about 245° C., and the optimum $Z^*$ will be slightly greater than 4.7.

The optimum temperature and overall chloriding effectiveness values may be determined, if necessary, by interpolation or extrapolation from plots of alkylene oxide concentration versus temperature and overall chloriding effectiveness values corresponding to the points used to construct the tangent line. The overall chloriding effectiveness values used to construct the tangent line may also themselves be interpolated or extrapolated from actual experimental data in order to define the temperature and overall chloriding effectiveness value $Z^*$ combination at the point of tangency for the relevant efficiency versus alkylene oxide concentration curve.

The slope of the tangent line intersecting the efficiency versus alkylene oxide concentration curves generated for a specific high efficiency silver catalyst at a plurality of temperatures is frequently no greater than about −1 percent efficiency/mole percent alkylene oxide, more frequently no greater than about −1.5 percent efficiency/mole percent alkylene oxide, and even more frequently no greater than about −2 percent efficiency/mole percent alkylene oxide. The slope is frequently at least about −5 percent efficiency/mole percent alkylene oxide, more frequently at least about −4.5 percent efficiency/mole percent alkylene oxide, and even more frequently at least about −4 percent efficiency/mole percent alkylene oxide. A slope of about −3 percent efficiency/mole percent alkylene oxide is most frequent. Put differently, in step 1012 of FIG. 3 $T_1$ and $Z_1^*$ are preferably selected such that the first derivative (i.e., the "slope" or ($\partial E/\partial C_{AO}$) when varying $Z^*$ at constant temperature, constant reactor inlet alkylene concentration and at a fixed process condition) falls within the foregoing ranges. The fixed process condition is one at which at least one variable selected from the group consisting of reactor inlet oxygen and carbon dioxide concentration, reactor pressure, and gas hourly space velocity is held constant, and more preferably is a condition at which each of these variables is held constant. In addition, the changes in $Z^*$ and T made in steps 1018 and 1020 are preferably made such that at the selected $Z^*$ and temperature, the efficiency toward the alkylene oxide varies with the reactor outlet concentration of alkylene oxide at constant temperature according to a function which has a first derivative (slope) at the selected temperature and $Z^*$ that is preferably no greater than about 1 percent efficiency/mole percent alkylene oxide, more preferably not greater than about 0 percent efficiency/mole percent alkylene oxide, and even more preferably no greater than about −1 percent efficiency/mole percent alkylene oxide. The slope at the selected temperature and $Z^*$ is preferably at least about −8 percent efficiency/mole percent alkylene oxide, more preferably at least about −7 percent efficiency/mole percent alkylene oxide, and even more preferably at least about −5 percent efficiency/mole percent alkylene oxide. In a preferred embodiment, the changes in $Z^*$ (step 1018) and T (step 1020) alter the efficiency to alkylene oxide (E) by an amount that differs from the optimum efficiency by preferably no more than about 0.5%, more preferably no more than about 0.4%, and most preferably no more than about 0.3%.

Figure 7C:
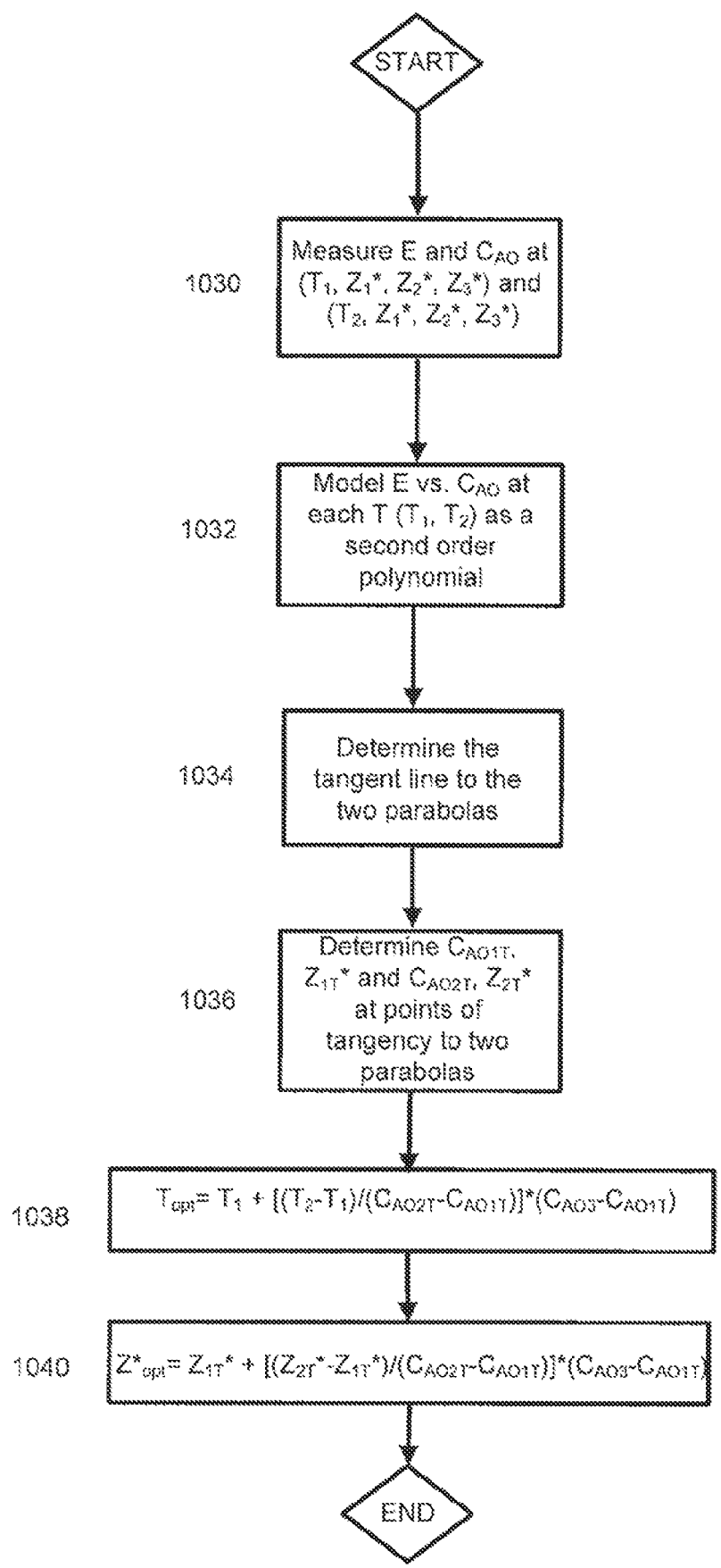
FIG. 7C is a flow chart depicting a third exemplary method of selecting a preferred initial operating condition of an alkylene oxide production process by optimizing an alkylene oxide production process carried out with a high efficiency catalyst by maximizing efficiency toward the alkylene oxide at a selected reactor outlet concentration of alkylene oxide.

As discussed above, in one preferred embodiment, the initial reaction temperature $T_1$ and initial overall catalyst chloriding effectiveness $Z_1^*$ are selected by an optimization process that involves maximizing the efficiency of process 20 to alkylene oxide concentration at the desired alkylene oxide production parameter (e.g., reactor outlet alkylene oxide concentration). An exemplary method of performing the optimization is provided in FIG. 7C. In accordance with the method, efficiency data (E) and reactor outlet alkylene oxide concentration data ($C_{AO}$) are collected at two temperatures ($T_1$ and $T_2$) and at least three overall catalyst chloriding effectiveness values ($Z_1^*$, $Z_2^*$, $Z_3^*$) for each of the temperatures (step 1030), which may be the same or different for each of the two temperatures. The reactor inlet alkylene concentration is preferably held constant and a fixed process condition is preferably employed as the temperature and $Z^*$ are varied. The fixed process condition is as described previously. The relationship between E and $C_{AO}$ at each temperature as $Z^*$ is varied among the three values $Z_1^*$, $Z_2^*$, and $Z_3^*$ is modeled as a second order polynomial, thereby yielding two parabolas with the parabola for the higher temperature ($T_2$) being shifted downward and to the left from the parabola for the lower temperature ($T_1$) on a plot of E vs. $C_{AO}$ (step 1032). The line that is tangent to both parabolas (e.g., $E=m(C_{AO})+b$, where m is the slope and b is the y-intercept) is then determined (step 1034), and the two reactor outlet alkylene oxide concentrations ($C_{AO1T}$ and $C_{AO2T}$) at the points of tangency for each parabola are determined (step 1036), as are the corresponding values of $Z^*$ at the points of tangency ($Z_{1T}^*$ and $Z_{2T}^*$) (step 1036). It may be necessary to interpolate between the values of $Z_1^*$, $Z_2^*$, and $Z_3^*$ from step 1030 to obtain $Z_{1T}^*$ and $Z_{2T}^*$. For an initial selected reactor outlet concentration of alkylene oxide, $C_{AO3}$, the optimal values of the reaction temperature and overall chloriding effectiveness can be calculated as follows:

$$T_{opt}=T_1+[(T_2-T_1)/(C_{AO2T}-C_{AO1T})]*(C_{AO3}-C_{AO1T}) \quad \text{(step 1038)} \tag{6}$$

$$Z^*_{opt}=Z_{1T}^*+[(Z_{2T}^*-Z_{1T}^*)/(C_{AO2T}-C_{AO1T})]*(C_{AO3}-C_{AO1T})\text{(step 1040)} \tag{7}$$

$T_{opt}$ and $Z^*_{opt}$ can then be used as $T_1$ and $Z_1^*$ in step 1012 of the method of FIG. 3.

The methods described herein can be used in open loop or closed loop processes. In one example of a closed loop system, depicted in FIG. 1, a controller 26 is provided which receives inputs from a reactor outlet concentration analyzer 27, a reactor feed concentration analyzer 42, an olefin feed flow meter 40, a gas phase promoter feed flow meter 44, and a net product flow meter 52. Controller 26 is preferably implemented in a computerized control system and also includes a CPU and a memory as well as outputs that are ultimately used to adjust control valves 30 and 38. Based on the received inputs, controller 26 determines the mole percentage of alkylene oxide in the reactor outlet 24 and an overall catalyst chloriding effectiveness (e.g., $Z^*$) for reactor feed 22.

Controller 26 also receives concentration data for chlorinated hydrocarbons such as ethyl chloride, vinyl chloride, and ethylene dichloride in reactor feed stream 22 from analyzer 42, as well as for the concentration of ethylene, ethane, and any other non-chlorinated hydrocarbons in reactor feed stream. The concentration data is then used to calculate the overall catalyst chloriding effectiveness (e.g., $Z^*$). Controller 26 may also receive a user entered set-point for the mole percent of alkylene oxide ($C_{AO}$) in reactor outlet 24 and/or the yield of alkylene oxide. Based on the user entered set point and data from analyzer 24, controller 26 determines if the concentration of alkylene oxide in reactor outlet 24 and/or the yield of alkylene oxide is within a pre-determined range of the user entered setpoint. When the alkylene oxide concentration and/or yield falls outside of the pre-determined range, controller 26 either adjusts the reaction temperature or the flow rate of the gas phase promoter (to change $Z^*$) to obtain the desired alkylene oxide concentration or yield. To adjust the flow rate of the gas phase promoter, controller 26 resets the set point of gas phase promoter flow controller 36, which receives flow data from flow meter 44 and manipulates control valve 38 to control the flow. To adjust the reaction temperature, controller 26 adjusts the set point of reaction temperature controller 34. Reaction temperature controller 34 receives a temperature signal from a reactor thermocouple and provides an output that resets the set point of coolant flow controller 32 (or a stream drum pressure controller in the case of a boiling water-cooled system). Coolant flow controller 32 receives coolant flow data from flow meter 31 and adjusts coolant control valve 30 to change the coolant flow rate and effect the temperature change.

As shown in FIG. 1, analyzer controller 50 may also be provided to regulate the olefin concentration in reactor feed 22. In the illustrated example, analyzer controller 50 receives compositional data from analyzer 42 indicating the amount of olefin in reactor feed 22. Analyzer controller 50 (which may have a user-entered set point for the olefin concentration in reactor feed stream 22) then resets the set point of flow controller 51 which receives flow data from flow meter 40 and manipulates control valve 12 to control the flow of fresh olefin feed. Analyzer controller 19 receives compositional data from analyzer 42 (or a separate analyzer) indicating the amount of oxygen in reactor feed 22. Analyzer controller 19 then resets the set point of oxygen flow controller 17 (which may be an air flow controller) which receives data from oxygen flow meter 21. Controllers 17, 19, 32, 34, 36, and 50 may be analog or digital and may be implemented in a computerized distributed control system. The illustrated control scheme is merely exemplary and is not meant to limit the scope of the present invention.

The methods used herein may be embodied in a set of computer readable instructions that are stored on a computer readable medium such as a magnetic disk or computer hard drive for use by controller 26. Controller 26 may be implemented in a number of ways, but the use of a computer control system is preferred.

Example 1

This example illustrates the adjustment of overall catalyst chloriding effectiveness to obtain a desired concentration of ethylene oxide without varying reaction temperature. A 70 cc sample of a high efficiency, rhenium promoted silver catalyst weighing 55.2 g is run in a laboratory autoclave reactor. The start up feed composition is 7.0 mole percent $O_2$, 30.0 mole percent $C_2H_4$, 2.8 ppmv ethyl chloride, 0.60 mole percent $C_2H_6$, 1.0 mole percent $CO_2$, and the balance $N_2$. The start up reaction temperature is 235° C., and the pressure is 2006 kPa (absolute). The total reactor inlet feed gas flow is 7.82 standard liters per minute (referenced to 0° C. and 1 atm).

The overall catalyst chloriding effectiveness $Z^*$ is calculated using the following formula:

$$Z^* = \frac{\text{ethyl chloride }(ppmv)}{(0.01^*\text{mole percent }C_2H_4 + \text{mole percent }C_2H_6)} \quad (8)$$

Figure 4:
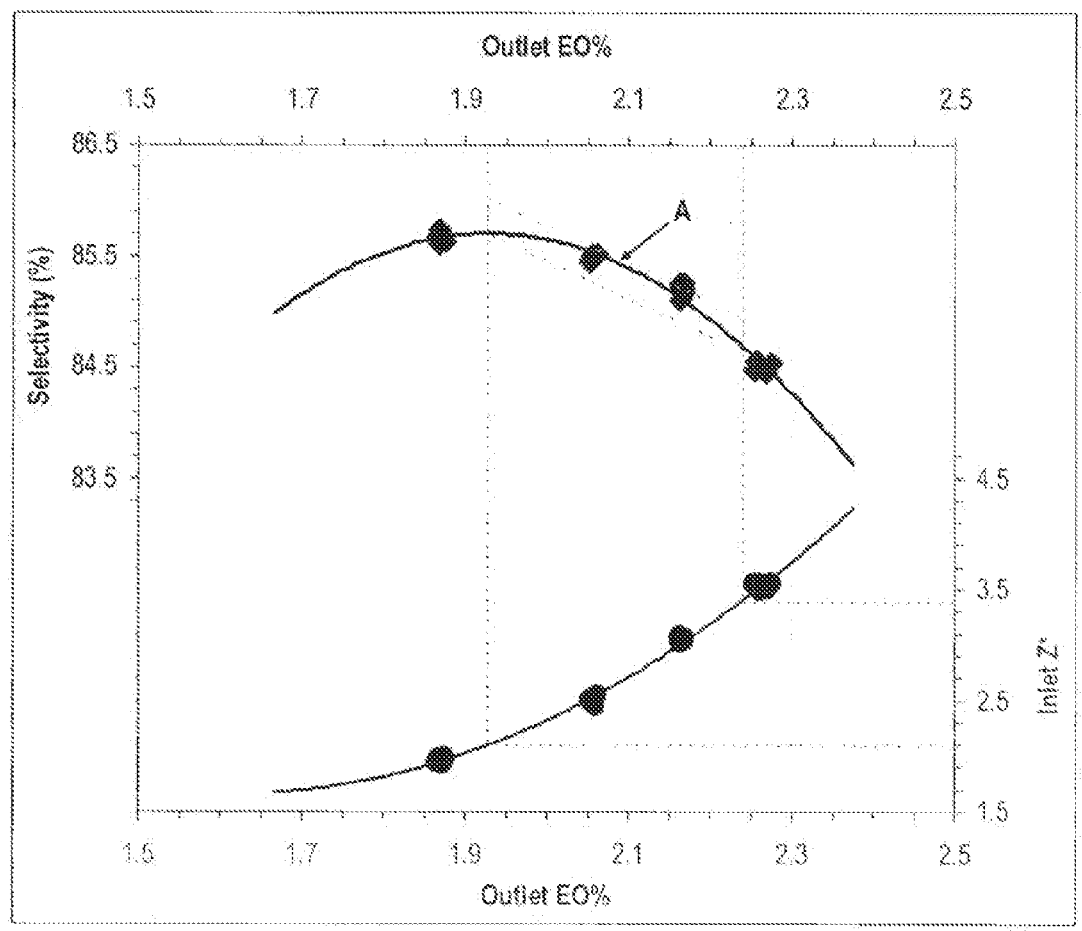
FIG. 4 is a graph depicting the effect of varying an overall chloriding effectiveness parameter value on the efficiency of a high efficiency catalyst, and the deviation of the process from an optimum condition as a result of the variation in overall catalyst chloriding effectiveness in an exemplary process for making ethylene oxide with a high efficiency catalyst.

From day 5 to day 9 of the test, the feed concentration of ethyl chloride is varied between 1.8 and 3.2 ppmv, while all other reaction conditions are kept constant. As a result, $Z^*$ varied from 2.0 to 3.5. FIG. 4 shows the catalyst efficiency (selectivity) versus ethylene oxide reactor outlet concentration (upper curve) and $Z^*$ (lower curve) after steady state is reached at each condition. Point A represents the point on the efficiency versus ethylene oxide concentration curve where the first derivative (slope) of the curve is about −3 percent efficiency/percent alkylene oxide, which is considered to represent the optimum combination of temperature and $Z^*$ for a reactor outlet ethylene oxide concentration of about 2.05 mole percent. As the outlet concentration of ethylene oxide is varied (by adjusting $Z^*$ at the specified reaction temperature), the efficiency will change in accordance with the upper curve. At an ethylene oxide outlet concentration of about 1.93 mole percent, the optimum combination of temperature and $Z^*$ would yield an efficiency of about 86.0%, as indicated by the upper dashed line. However, if $Z^*$ is adjusted to 2.1 without changing the reaction temperature in order to achieve an ethylene oxide concentration of 1.93 mole percent, the actual efficiency will be about 85.7%, a loss (deviation from optimum) of only about 0.3%. Similarly, at a selected ethylene oxide outlet concentration of about 2.24 mole percent, the optimum combination of $Z^*$ and reaction temperature would result in an efficiency of about 84.9%. However, if $Z^*$ is changed to 3.4 without changing the reaction temperature in order to adjust $C_{AO}$ to 2.24 mole percent, the actual efficiency will be about 84.7 percent, a loss (deviation from optimum) of only about 0.2 percentage points. Thus, in this example, $Z^*$ can be used to adjust ethylene oxide productivity without also adjusting temperature and without incurring an efficiency penalty of more than 0.3 percentage points, illustrating that the ethylene oxide production rate can be adjusted and maintained by adjusting $Z^*$ without changing reaction temperature and without any substantial loss in efficiency.

Example 2

This example shows the operation of the process described in the previous example after continued operation at days 17-21. In this example, the reaction temperature is 245° C., and the inlet concentration of ethyl chloride is varied from 2.3 to 3.6 ppmv while all other reaction conditions described in Example 1 are held constant. The resulting data are presented in Table 1:

TABLE 1

| Age day | Inlet ECL ppm | Inlet $Z^*$ | Outlet EO % | Efficiency % |
| --- | --- | --- | --- | --- |
| 17 | 2.3 | 2.6 | 2.14 | 84.8 |
| 18 | 2.3 | 2.5 | 2.10 | 84.8 |
| 19 | 3.6 | 4.0 | 2.45 | 84.6 |
| 20 | 3.6 | 4.0 | 2.45 | 84.5 |
| 21 | 3.2 | 3.5 | 2.33 | 84.6 |

As Table 1 indicates, adjusting the ethyl chloride concentration from 2.3 ppmv to 3.6 ppmv causes $Z^*$ to vary from 2.6 to 4.0, and increases the ethylene oxide outlet concentration from 2.14 mole percent to 2.45 mole percent. The efficiency (selectivity) is relatively insensitive to changes in $Z^*$, varying only by 0.3 percentage points. Thus, at the selected process conditions, $Z^*$ can be used to adjust ethylene oxide outlet concentration without adjusting reaction temperature and without significantly sacrificing efficiency.

Example 3

This example illustrates the applicability of the method of adjusting either $Z^*$ or T to control ethylene oxide productivity for an aged catalyst. Ethylene, oxygen, and ethyl chloride are reacted at a temperature of 245° C. over a high efficiency, rhenium-promoted, silver catalyst that has aged about 330 days. The catalyst contains 29.4 weight percent Ag and is prepared with a target formulation of 1000 ppm Cs, 504 ppm Re, 195 ppm $SO_4$ and 41 ppm Mn on an alpha-alumina support having the following properties:

| | |
| --- | --- |
| surface area | 0.88 m²/g |
| total pore volume | 0.566 cc/g |
| water absorption | 53.1% |

Figure 5:
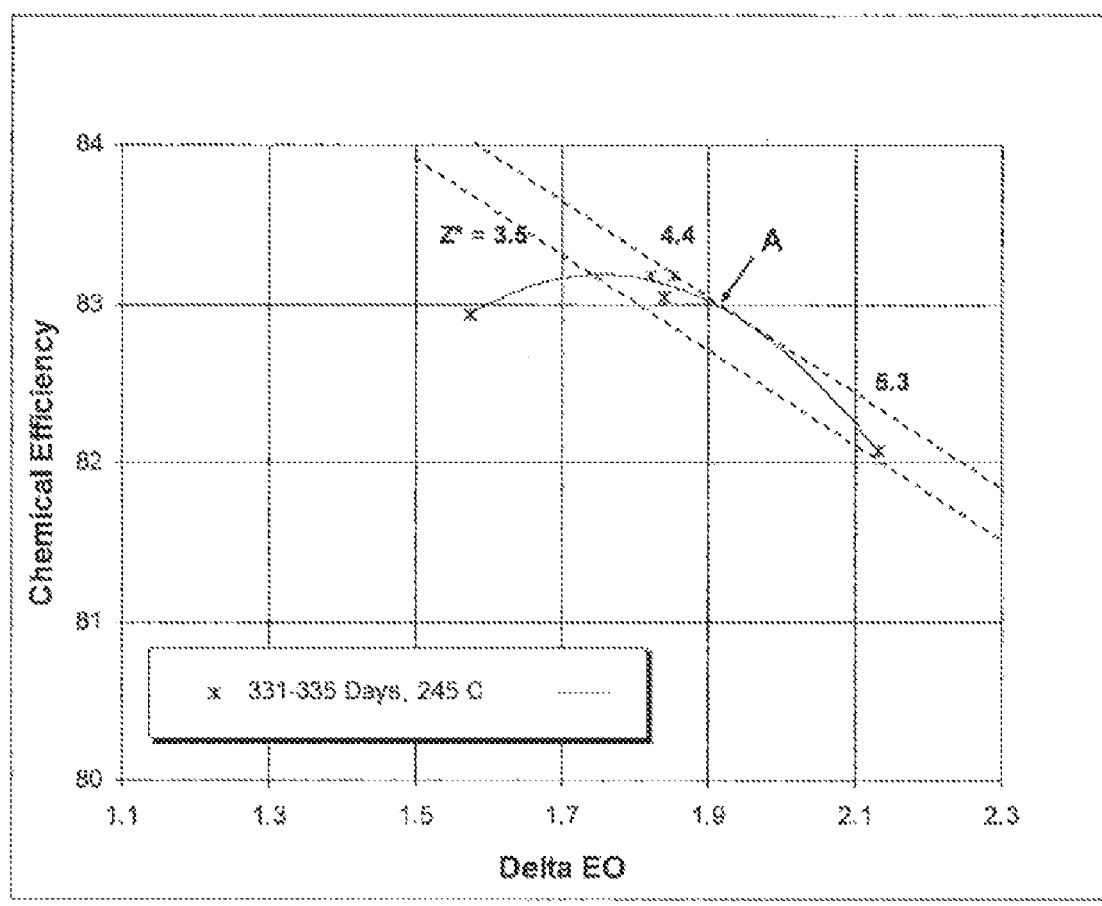
FIG. 5 is a graph depicting the effect of varying an overall catalyst chloriding effectiveness parameter value on catalyst selectivity (efficiency) in an exemplary process for making ethylene oxide using a high efficiency catalyst.

A tubular reactor having 29.5-mm inside diameter is charged to a depth of 7.62 meters (4081.8 grams) of this catalyst. The feed composition is 7.0 mole percent $O_2$, 30.0 mole percent $C_2H_4$, 3.0 mole percent $CO_2$, and 0.15 mole percent $C_2H_6$. The reactor pressure is 2100 kPa (absolute), and the gas hourly space velocity is 4700 hr$^{-1}$. Ethyl chloride concentration is varied to yield $Z^*$ values of 3.5, 4.4, and 5.3, and ethylene oxide outlet concentrations and the corresponding efficiencies are determined. The observed data points are shown with an "x" in FIG. 5 and are fit to a quadratic equation to yield the parabola shown in FIG. 5. Point A on FIG. 5 represents the point on the efficiency versus ethylene oxide concentration curve where the first derivative (slope) of the curve is about −3 percent efficiency/mole percent ethylene oxide. The catalyst age for the indicated data points ranges from 331-335 days. As FIG. 5 indicates, varying Z* from about 4 to about 5.3 to adjust the ethylene oxide outlet concentration from 1.7 mole percent to 2.1 mole percent yields an efficiency that deviates from the optimum (as indicated by the upper dashed line) by no more than about 0.3 percentage points.

Example 4

Figure 6:
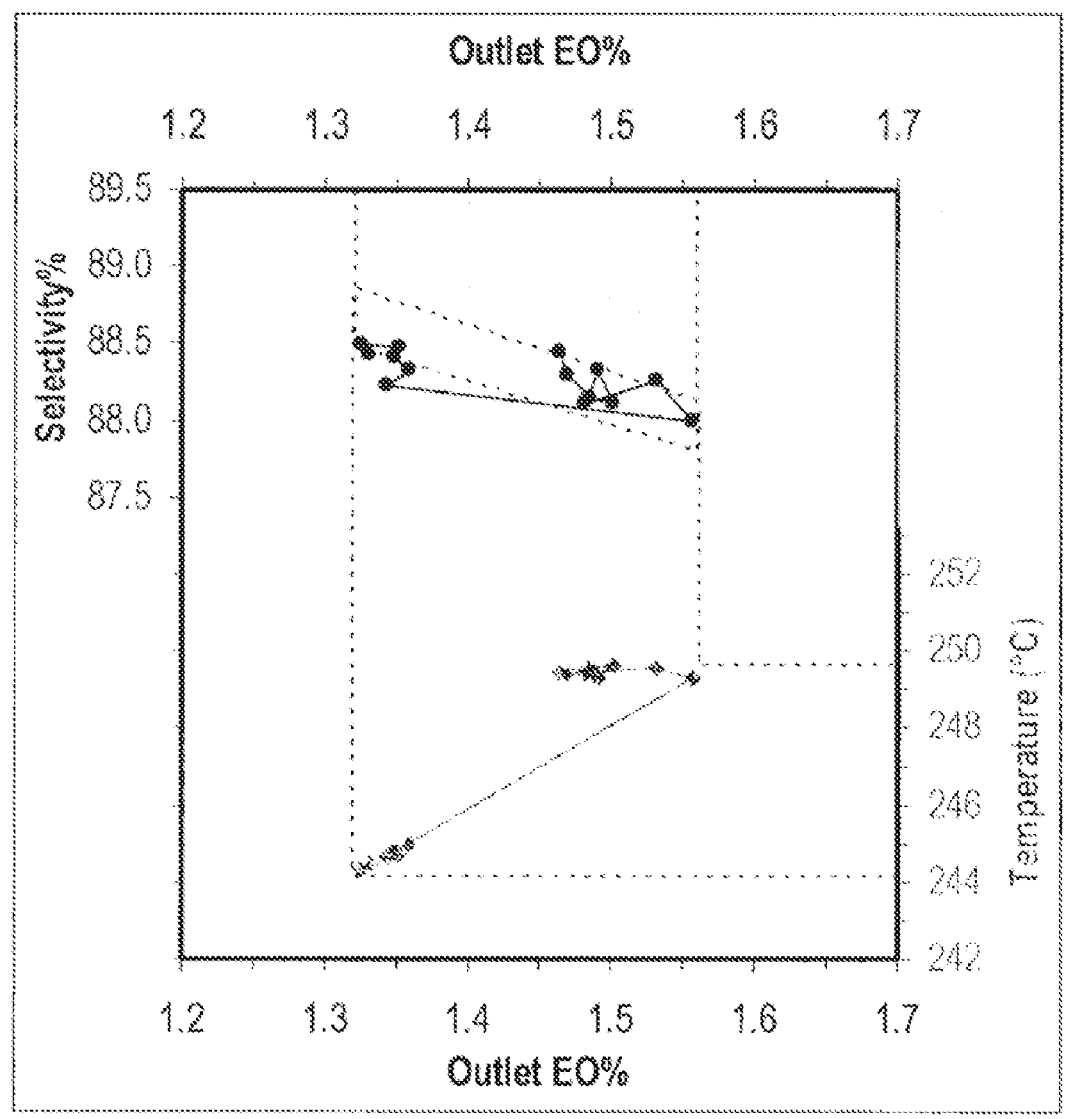
FIG. 6 is a graph depicting the effect of varying reaction (inlet coolant) temperature on catalyst efficiency in an exemplary process for making ethylene oxide using a high efficiency catalyst.

This example illustrates the use of reaction temperature to adjust ethylene oxide outlet concentration while Z* is held constant for a middle-of-life catalyst. A 30-50 mesh size, high efficiency, rhenium-promoted silver catalyst in an amount of 0.75 g is placed in a 3.05 mm (ID) stainless steel tube reactor. A feed gas comprising $O_2$ (8.8 mole percent), $C_2H_4$ (34.3 mole percent), ethyl chloride (5.9 ppmv), $C_2H_6$ (0.61 mole percent), $CO_2$ (1.5 mole percent), and balance $N_2$ is fed to the reactor. The reactor pressure is 1406 kPa (absolute), and the feed mixture flow rate is 158 standard cc per minute (referenced to 0° C. and 1 atm). The corresponding overall catalyst chloriding effectiveness, Z*, is 6.1. FIG. 6 shows the daily-average efficiency as a function of outlet ethylene oxide concentration in mole percent several days before and several days after the reaction temperature is increased from about 245° C. to about 250° C. on day 107. The dashed lines have a slope of approximately −3 percent efficiency/mole percent ethylene oxide, and the vertical spacing between the lines represents an efficiency (selectivity) loss of about 0.3 percentage points.

As shown in FIG. 6, the outlet ethylene oxide concentration varies from about 1.33 mole percent to about 1.55 mole percent in response to the change in temperature, and the efficiency varies from about 88.5 percent to about 88.0 percent. Thus, this example illustrates the reaction temperature can be varied to obtain a desired alkylene oxide outlet concentration without varying the overall catalyst chloriding effectiveness parameter, Z*, and without incurring significant losses in efficiency.

Example 5

As discussed above, alkylene oxide production parameters that may be used with the methods described herein include oxygen conversion. This example illustrates the adjustment of overall catalyst chloriding effectiveness (Z*) at constant temperature to achieve a desired oxygen conversion value.

In accordance with the example, an alpha-alumina supported silver catalyst is prepared using cesium, sodium, lithium, rhenium, sulfate, and manganese compounds as promoters. A sample of this catalyst is charged to a tubular reactor configured so that a portion of the reactor outlet gas is recycled back to the reactor inlet after addition of fresh feed components. The reactor is started up and the catalyst is operated under a range of process conditions for the first 24 days. Because multiple Cl-containing species may be present in the feed stream due to recycle from the reactor outlet, the overall catalyst chloriding effectiveness Z* is calculated using the following formula:

$$Z^* = (ECL + 2^*EDC + VCL)/(C2H6 + 0.01^*C2H4) \quad (9)$$

wherein ECL, EDC, and VCL are the concentrations in ppmv of ethyl chloride, ethylene dichloride, and vinyl chloride, respectively, in the reactor feed stream, C2H6 and C2H4 are the concentrations in mole percent of ethane and ethylene, respectively, in the reactor feed stream.

Between days 25 and 30 of the run, the following conditions are maintained: inlet feed concentrations of 35.0 mole percent ethylene, 8.5 mole percent oxygen, 1.1 mole percent carbon dioxide, 0.6 mole percent ethane; inlet coolant temperature of 230.0° C.; inlet pressure of 2140 kPa absolute (295 psig); and a gas hourly space velocity of 5100 ($hr^{-1}$). On Day 25, the overall catalyst chloriding effectiveness value Z* is 2.9. The observed efficiency is 88.4% at an oxygen conversion of 23.0%.

Over the following three days of operation, the oxygen conversion declines to 22.3%. Consequently, in order to restore the target oxygen conversion of 23.0%, the feed rate of ethyl chloride is adjusted for Day 29 to increase the overall catalyst chloriding effectiveness value Z* to 3.1. As a result of this change, the oxygen conversion is increased to 23.2% and the efficiency is 88.3%.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A process for manufacturing an alkylene oxide by reacting a feed gas comprising an alkylene, oxygen, and at least one organic chloride over a high efficiency silver catalyst to yield a reaction product comprising the alkylene oxide, the process comprising:
    operating the process at an initial overall catalyst chloriding effectiveness value and an initial reaction temperature to yield an initial value of an alkylene oxide production parameter;
    selecting a desired value of the alkylene oxide production parameter; and
    adjusting the overall catalyst chloriding effectiveness within a selected range of overall catalyst chloriding effectiveness values, while maintaining the reaction temperature at a substantially constant value, to yield the desired value of the alkylene oxide production parameter.

2. The process for manufacturing an alkylene oxide of claim 1, wherein when the overall catalyst chloriding effectiveness is within the selected range of overall catalyst chloriding effectiveness values, the reaction temperature is within a selected range of reaction temperatures, and the overall chloriding effectiveness is varied at a substantially constant temperature, substantially constant reactor inlet alkylene concentration, and a substantially fixed process condition, the process has an efficiency toward the alkylene oxide that varies with the concentration of alkylene oxide in the reaction product according to a function, and the slope of the function ranges from about 1 percent efficiency/mole percent alkylene oxide to about −8 percent efficiency/mole percent alkylene oxide.

3. The process for manufacturing an alkylene oxide of claim 1, wherein the process has an optimum efficiency that varies with both the reaction temperature and the alkylene oxide concentration in the reaction product, and when the overall catalyst chloriding effectiveness is within the selected range of overall catalyst chloriding effectiveness values and the reaction temperature is within a selected range of reaction temperatures, the step of adjusting the overall catalyst chloriding effectiveness yields an efficiency toward the alkylene oxide that varies from the optimum efficiency by no more than about 0.5 percent.

4. The process for manufacturing an alkylene oxide of claim 3, wherein the optimum efficiency is an optimum efficiency at a substantially constant reactor inlet alkylene concentration and a substantially fixed process condition.

5. The process for manufacturing an alkylene oxide of claim 1, wherein the alkylene oxide production parameter is selected from the group consisting of alkylene oxide concentration, alkylene oxide yield, alkylene oxide production rate, alkylene oxide production rate/catalyst volume, alkylene conversion, and oxygen conversion.

6. The process for manufacturing an alkylene oxide of claim 1, wherein the overall catalyst chloriding effectiveness is represented by the formula:

$$Z^* = \frac{\text{ethyl chloride equivalent }(ppmv)}{\text{ethane equivalent (mole percent)}}$$

wherein the ethyl chloride equivalent is the total concentration in ppmv of ethyl chloride which provides substantially the same catalyst chloriding effectiveness of the at least one organic chloride in the feed gas at the concentration of the at least one organic chloride in the feed gas; and the ethane equivalent is the total concentration in mole percent of ethane which provides substantially the same dechloriding effectiveness as the non-chloride containing hydrocarbons in the feed gas at the concentration of the non-chloride containing hydrocarbons in the feed gas.

7. The process for manufacturing an alkylene oxide of claim 6, wherein the at least one organic chloride is selected from the group consisting of ethyl chloride, ethylene dichloride, and vinyl chloride, and the ethyl chloride equivalent has the following formula:

ethyl chloride equivalent$(ppmv)$=$ECL$+$2EDC$+$VCL$ wherein, ECL is the concentration of ethyl chloride in the feed gas in ppmv, EDC is the concentration of ethylene dichloride in the feed gas in ppmv, and VCL is the concentration of vinyl chloride in the feed gas in ppmv.

8. The process for manufacturing an alkylene oxide of claim 6, wherein the non-chloride containing hydrocarbons in the feed gas comprise at least one selected from the group consisting of ethylene and ethane, and the ethane equivalent has the following formula:

ethane equivalent(mole percent)=$C_2H_6$+0.01$C_2H_4$ wherein, $C_2H_6$ is the concentration of ethane in the feed gas in mole percent, and $C_2H_4$ is the concentration of ethylene in the feed gas in mole percent.

9. The process for manufacturing an alkylene oxide of claim 6, wherein the selected range of $Z^*$ is from about 1 to about 20.

10. The process for manufacturing an alkylene oxide of claim 6, wherein the step of adjusting the overall catalyst chloriding effectiveness comprises adjusting $Z^*$ by no more than about 2.0.

11. The process for manufacturing an alkylene oxide of claim 1, wherein the alkylene oxide is ethylene oxide and the alkylene is ethylene.

12. The process for manufacturing an alkylene oxide of claim 1, wherein the at least one organic chloride is selected from the group consisting of ethyl chloride, methyl chloride, ethylene dichloride, vinyl chloride, and mixtures thereof.

13. The process for manufacturing an alkylene oxide of claim 1, wherein the initial reaction temperature and the initial overall catalyst chloriding effectiveness comprise an optimized combination of the overall catalyst chloriding effectiveness and reaction temperature based on one or more variables selected from the group consisting of efficiency, catalyst activity, and alkylene oxide concentration in the reaction product.

14. The process for manufacturing an alkylene oxide of claim 1, wherein the initial overall catalyst chloriding effectiveness is selected to provide the maximum efficiency toward the alkylene oxide at the initial reaction temperature and the initial alkylene oxide production parameter.

15. The process for manufacturing an alkylene oxide of claim 1, wherein the process further comprises selecting an initial alkylene oxide production parameter value, and selecting the initial reaction temperature and the initial overall catalyst chloriding effectiveness value to obtain a maximum efficiency toward the alkylene oxide at the selected initial alkylene oxide production parameter value.

16. The process for manufacturing an alkylene oxide of claim 1, wherein when an overall chloriding effectiveness is varied, the process has an alkylene oxide efficiency maximizing combination of reaction temperature and overall chloriding effectiveness at a fixed reactor inlet alkylene concentration and fixed process condition, and the maximized efficiency varies with the concentration of the alkylene oxide in the reaction product according to a linear relationship, the linear relationship has a slope ranging from about −1 percent efficiency toward the alkylene oxide/mole percent alkylene oxide to about −5 percent efficiency toward the alkylene oxide/mole percent alkylene oxide, and the adjusting step yields an efficiency toward the alkylene oxide that varies from the efficiency defined by the linear relationship by an amount that is no greater than 0.5%.

17. The process for manufacturing an alkylene oxide of claim 1, wherein the high efficiency silver catalyst comprises a rhenium promoter.

* * * * *